(12) United States Patent
Hong et al.

(10) Patent No.: US 7,350,916 B2
(45) Date of Patent: Apr. 1, 2008

(54) INTRAOCULAR LENS

(75) Inventors: Xin Hong, Arlington, TX (US); Jihong Xie, Fort Worth, TX (US); Stephen J. Van Noy, Fort Worth, TX (US); Dan Stanley, Midlothian, TX (US); Mutlu Karakelle, Forth Worth, TX (US); Xiaoxiao Zhang, Forth Worth, TX (US); Michael J. Simpson, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 133 days.

(21) Appl. No.: 11/397,332

(22) Filed: Apr. 4, 2006

(65) Prior Publication Data

US 2006/0244904 A1   Nov. 2, 2006

Related U.S. Application Data

(60) Provisional application No. 60/668,520, filed on Apr. 5, 2005.

(51) Int. Cl.
*G02C 7/02* (2006.01)
*A61F 2/16* (2006.01)

(52) U.S. Cl. .................. 351/159; 351/212; 623/6.11; 623/6.43

(58) Field of Classification Search ............. 351/159, 351/205, 212, 247; 623/6.11, 6.43–6.46, 623/6.54
See application file for complete search history.

(56) References Cited

U.S. PATENT DOCUMENTS

| | | | |
|---|---|---|---|
| 4,195,919 A | 4/1980 | Shelton | |
| 4,504,982 A | 3/1985 | Burk | |
| 5,092,880 A | 3/1992 | Ohmi | |
| 5,171,319 A | 12/1992 | Keates et al. | |
| 5,217,489 A | 6/1993 | Van Noy et al. | |
| 5,922,821 A | 7/1999 | LeBoeuf et al. | |
| 6,096,077 A | 8/2000 | Callahan et al. | |
| 6,353,069 B1 | 3/2002 | Freeman et al. | |
| 6,786,603 B2 | 9/2004 | Altmann | |
| 6,797,003 B1 | 9/2004 | Blake et al. | |

(Continued)

FOREIGN PATENT DOCUMENTS

EP     0 472 291     2/1992

(Continued)

OTHER PUBLICATIONS

Atchison, D.A.; "Optical design of PMMA IOLs", J Cataract Refr Surg, vol. 16:178 1990.

(Continued)

*Primary Examiner*—Huy K Mai
(74) *Attorney, Agent, or Firm*—Jeffrey S. Schira

(57) ABSTRACT

In one aspect, the present invention provide an ophthalmic lens (e.g., an IOL) that includes an optic having an anterior optical surface and a posterior optical surface, where the optic provides an optical power in a range of about 16 D to about 25 D as measured in a medium having an index of refraction substantially similar to that of the eye's aqueous humor (e.g., about 1.336). At least one of the optical surfaces is characterized by an aspherical base profile such that the optic exhibits a negative spherical aberration in a range of about −0.202 microns to about −0.190 microns across the power range.

18 Claims, 4 Drawing Sheets

U.S. PATENT DOCUMENTS

| | | |
|---|---|---|
| 2001/0051826 A1 | 12/2001 | Bogaert et al. |
| 2002/0105617 A1 | 8/2002 | Norrby et al. |
| 2002/0122153 A1 | 9/2002 | Piers et al. |
| 2004/0088050 A1* | 5/2004 | Norrby et al. ............. 623/6.11 |
| 2004/0156014 A1 | 8/2004 | Piers et al. |
| 2005/0203619 A1 | 9/2005 | Altmann |
| 2006/0030938 A1 | 2/2006 | Altmann |
| 2006/0232743 A1* | 10/2006 | Legerton ................... 351/246 |

FOREIGN PATENT DOCUMENTS

| | | |
|---|---|---|
| EP | 0742466 | 11/1996 |
| JP | 04 126144 | 4/1992 |
| WO | WO 01/89424 | 11/2001 |
| WO | WO 2004/034129 | 4/2004 |
| WO | WO- 00/28368 | 8/2004 |
| WO | WO- 2004/068214 | 8/2004 |
| WO | WO-2004090611 | 10/2004 |
| WO | WO- 2005/098518 | 10/2005 |

OTHER PUBLICATIONS

Atchison, D.A.; "Design of aspheric IOLs", Ophthal Physiol Optics, vol. 11:137 1991.

P. M. Kiely, et. al. "The mean shape of the human cornea," Optica Acta, vol. 29:1027 1982.

P. M. Kiely, et. al. "Meridional variations of corneal shape," AM. J. Optom. Physiol. Optics, vol. 61:619 1984.

Michel Guillon et. al., "Corneal topography: a clinical model," Ophthal. Physiol. Opt. vol. 6: 47 1986.

Stephen J. Bogan et. al., "Classification of normal cornea topography based on computer-assisted videokeratography," Arch Ophthalmo. vol. 108:945 1990.

Atchison, D.A.; "Third-order aberrations of pseudophakic eyes", Ophthalmic and Physiological Optics, vol. 9(2):205-211, 1989.

* cited by examiner

INTRAOCULAR LENS

RELATED APPLICATION

The present application claims priority to U.S. Provisional Patent Application Ser. No. 60/668,520 entitled "Intraocular Lens," filed on Apr. 5, 2005, which is herein incorporated by reference.

A U.S. patent application entitled "Optimal IOL Shape Factors for Human Eyes," assigned to the assignee of the present application, and concurrently filed herewith is also herein incorporated by reference.

BACKGROUND

The present invention is directed generally to ophthalmic lenses, and more particularly, to intraocular lenses having aspherical profiles.

Generally speaking, asphericity describes the extent to which a curved, three-dimensional surface deviates from an ideal spherical shape. In the case of a lens, the asphericity can manifest itself on the anterior surface, the posterior surface or in the combined effect of both surfaces as they refract light passing through the lens.

The principal optical components of the natural eye are the cornea, which forms the anterior of the eye, and the natural crystalline lens that lies within the eye. The cornea is the first component of the ocular system and provides roughly two-thirds of the focusing power of the system. The crystalline lens provides the remaining focusing capability of the eye.

An intraocular lens (IOL) is typically implanted in a patient's eye during cataract surgery to compensate for the lost optical power when the natural lens is removed. In many cases, however, the optical performance of the IOL may be degraded by inherent corneal aberrations. The human cornea generally exhibits a positive spherical aberration, which is typically offset by a negative spherical aberration of the natural crystalline lens. If this positive spherical aberration of the cornea is not accounted for, it will adversely affect the focusing of light by the combined system of cornea and an implanted IOL.

Intraocular lenses that compensate for spherical aberration are known. However, there is no consensus on how, or the extent to which, an IOL should compensate for the corneal aberration. Accordingly, there is a need for improved ophthalmic lenses, and particularly, for improved IOLs that address the issue of spherical aberration.

SUMMARY

The present invention generally provides ophthalmic lenses that exhibit a selected degree of negative spherical aberration over a power range (e.g., about 16 D to about 25 D) so as to compensate for the positive spherical aberration of the cornea. In many embodiments, one or more lens surfaces are configured to have aspherical profiles so as to cause the lens to exhibit a desired degree of negative spherical aberration.

In one aspect, the present invention provides an ophthalmic lens (e.g., an IOL) that includes an optic having an anterior optical surface and a posterior optical surface, where the optic provides an optical power in a range of about 6 to about 34 D, and more preferably in a range of about 16 D to about 25 D as measured in a medium having an index of refraction substantially similar to that of the eye's aqueous humor (e.g., about 1.336). At least one of the optical surfaces is characterized by an aspherical base profile such that the optic exhibits a negative spherical aberration in a range of about −0.202 microns to about −0.190 microns across the power range. The spherical aberration values, which are defined as root mean square (RMS) of the aberration, are measured over a 6 mm pupil, when implanted in a human eye (or a model eye), which can correspond to a lens aperture size of about 5 mm for an ophthalmic lens implanted in the human capsular bag. Unless otherwise indicated, the spherical aberration values recited herein are based on these criteria, and hence, for ease of description, the RMS definition and the 6 mm qualification will be omitted in connection with spherical aberration values recited in the sections that follow.

In a related aspect, the aspherical base profile can be characterized by a conic constant in a range of, for example, about −73 to about −27 with the power of lens lying in a range of about 16 D to about 25 D.

In another aspect, the aspherical base profile can be defined according to the following relation:

$$z = \frac{cr^2}{1+[1-(1+k)c^2r^2]^{\frac{1}{2}}} + a_1 r^2 + a_2 r^4 + a_3 r^6$$

wherein, z denotes a sag of the surface at a radial distance r from an optical axis of the lens, c denotes curvature of the surface at its apex (at the intersection of the optical axis with the surface)

k denotes a conic constant, $a_1$ denotes a second order aspheric coefficient, $a_2$ denotes a fourth order aspheric coefficient, and $a_3$ denotes a sixth order aspheric coefficient.

In a related aspect, the optic can provide an optical power in a range of about 6 D to about 30 D, and an aspheric surface of the lens can be characterized by the above relation with c ranging from about 0.0152 $mm^{-1}$ to about 0.0659 $mm^{-1}$, k ranging from about −1162 to about −19, $a_1$ ranging from about −0.00032 $mm^{-1}$ to about −0.00020 $mm^{-1}$, $a_2$ ranging from about −0.0000003 (minus 3×10$^{-7}$) $mm^{-3}$ to about −0.000053 (minus 5.3×10$^{-5}$) $mm^{-3}$, and $a_3$ ranging from about 0.0000082 (8.2×10$^{-6}$) $mm^{-5}$ to about 0.000153 (1.53×10$^{-4}$) $mm^{-5}$.

In another aspect, the optic can provide an optical power in a range of about 16 D to about 25 D, and an aspheric surface of the lens can be characterized by the above relation with c ranging from about 0.0369 (1/27.1) $mm^{-1}$ to about 0.0541 (1/18.5) $mm^{-1}$, k ranging from about −73 to about −27, $a_1$ ranging from about −0.000209 $mm^{-1}$ to about −0.000264 $mm^{-1}$, $a_2$ ranging from about −0.0000297 $mm^{-3}$ to about −0.0000131 $mm^{-3}$, and $a_3$ ranging from about 0.00000978 $mm^{-5}$ to about 0.00000846 $mm^{-5}$.

In another aspect, the optic of the ophthalmic lens exhibits a shape factor in a range of about −0.016 to about 0.071. Further, the principal plane of the optic can exhibit an offset change in a range of about −0.019 mm to about +0.018 mm relative to a desired lens plane such as the plane defined by the two haptics—optic junctions with the optic, with the optic providing an optical power in a range of about 16 D to about 25 D.

The ophthalmic lens can be formed of a variety of materials, which are preferably biocompatible. By way of example, the optic can be formed of a soft acrylic polymeric material. Other examples of suitable materials include, without limitation, hydrogel and silicone polymeric materials.

In another aspect, an ophthalmic lens is disclosed that includes an optic having an anterior surface and a posterior surface, which cooperatively provide an optical power in a range of about 16 D to about 25 D. At least one of the surfaces exhibits an aspheric base profile so as to provide a negative spherical aberration for countering, upon implantation in the eye, a positive spherical aberration of the cornea such that a residual spherical aberration of a combined optical system of the lens and cornea reaches a desired value. The human corneal spherical aberration can range from about 0.194 to 0.284 microns—a variation in a range of 0.09 microns. To avoid overcorrection, the spherical aberration of the lens (e.g., from about −0.202 microns to about −0.190 microns) can be targeted to correct the low end of the corneal spherical aberration. As a result, in some embodiments, the residual spherical aberration of the combined optical system of the lens and cornea can be a positive value less than about 0.14 microns, e.g., in a range from about +0.006 to about +0.09 microns (as discussed below, even a +0.14 micron spherical aberration can be beneficial). The residual spherical aberration can be measured, e.g., in a model eye comprising the ophthalmic lens and a cornea model exhibiting a selected positive spherical aberration (e.g., an average spherical aberration of human cornea). Alternatively, the residual spherical aberration can be measured in a human eye in which the ophthalmic lens is implanted.

In a related aspect, in the above ophthalmic lens, the aspheric base profile is characterized by a conic constant in a range of about −73 to about −27. Further, the lens can exhibit a shape factor in a range of about −0.016 to about 0.071.

In another aspect, an ophthalmic lens (e.g., an IOL) is disclosed that includes an optic having an anterior surface and a posterior surface, where the optic provides an optical power in a range of about 16 D to about 25 D. The optic includes a principal plane exhibiting an offset change in a range of about −0.019 mm to about +0.018 mm from a selected plane of the optic. Further, at least one of the surfaces is characterized by an aspherical base profile such that the optic exhibits a negative spherical aberration in a range of about −0.202 microns to about −0.190 microns across said power range.

In a related aspect, the above ophthalmic lens includes a pair of haptics coupled thereto, and the principal plane exhibits the aforementioned offset change (in a range of about −0.019 mm to about +0.018 mm) relative to a plane defined by the junctions of the haptics with the optic.

Further understanding of the invention can be obtained by reference to the following detailed description in conjunction with the associated drawings, which are discussed briefly below.

DETAILED DESCRIPTION OF THE PREFERRED EMBODIMENTS

The present invention relates generally to ophthalmic lenses (e.g., intraocular lenses) that exhibit a selected degree of negative spherical aberration so as to counter the positive spherical aberration of the cornea (e.g., an average positive spherical aberration of the cornea of a population of patients), thereby providing an enhanced image contrast.

Figure 1:
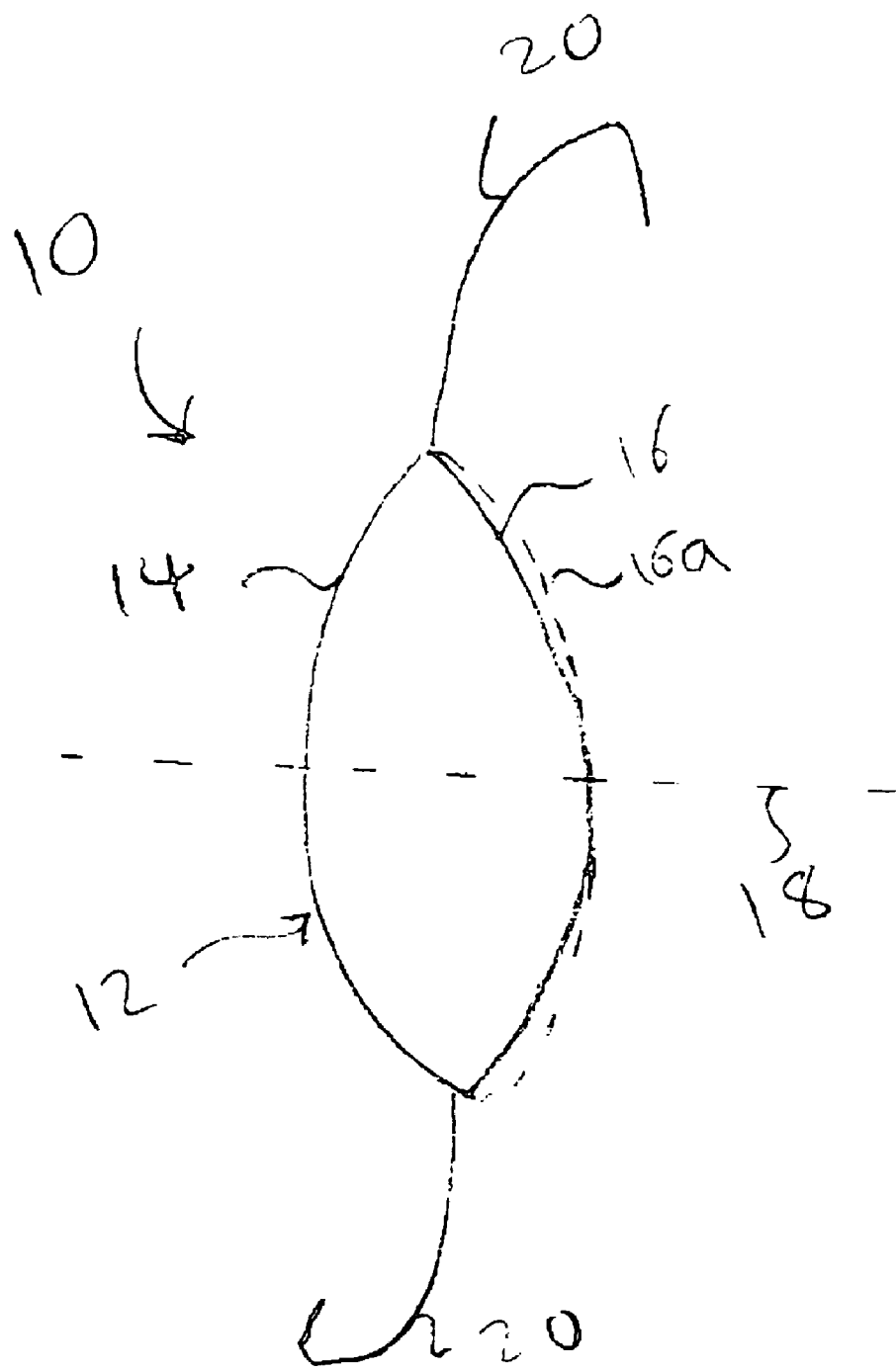
FIG. 1 is a schematic side view of an IOL according to one embodiment of the invention.

With reference to FIG. 1, an IOL 10 in accordance with one embodiment of the invention includes an optic 12 having an anterior optical surface 14 and a posterior optical surface 16. In this embodiment, the anterior and posterior optical surfaces 14 and 16 are symmetrically disposed about an optical axis 18. In other embodiments, one or both surfaces can exhibit some degree of asymmetry relative to the optical axis 18. The exemplary lens 10 further includes radially extending fixation members or haptics 20 for its placement in a patient's eye. While in this embodiment the optic 12 is formed of a soft acrylic polymer (e.g., a material used to form commercially available lenses sold under the trademark Acrysof®), in other embodiments, it can be formed of any other suitable biocompatible material, such as silicone or hydrogel. The fixation members 20 can also be integrally formed with the optic and from the same material (a "single piece" lens), or formed separately from the optic of suitable polymeric materials, such as polymethylmethacrylate, polypropylene and the like (a "multi-piece" lens). By way of further examples, U.S. Pat. No. 6,416,550, which is herein incorporated by reference, discloses materials suitable for forming the IOL 10.

In this embodiment, the optical surfaces 14 and 16 have generally convex shapes, although other shapes (e.g., concave or flat) can also be employed for those surfaces to form, e.g., plano-convex or plano-concave lenses. The term "intraocular lens" and its abbreviation "IOL" are used herein interchangeably to describe lenses that are implanted into the interior of an eye to either replace the eye's natural lens or to otherwise augment vision regardless of whether or not the natural lens is removed. Intracorneal lenses and phakic lenses are examples of lenses that may be implanted into the eye without removal of the natural lens.

In this embodiment, the curvatures of the optical surfaces 14 and 16, together with the index of refraction of the material forming the optic, are chosen such that the optic would provide a refractive optical power in a range of about 16 D to about 25 D. By way of example, in some embodiments, the lens exhibits an optical power in this range when placed in a medium having an index of refraction of about 1.336 (e.g., the aqueous humor of the eye).

With continued reference to FIG. 1, while the anterior surface 14 of the optic 12 is characterized by a substantially spherical base profile, the posterior surface 16 is characterized by an aspherical base profile. That is, the posterior surface 16 includes a base profile that is substantially coincident with a putative spherical profile 16a (depicted by dashed lines) at small radial distances from the optical axis but exhibits increasing deviation from that spherical profile as the radial distance from the optical axis increases. In many embodiments, the asphericity of the posterior surface is selected such that the optic exhibits a negative spherical aberration in a range of about −0.202 (minus 0.202) microns to about −0.190 (minus 0.190) microns. A lens with such a negative spherical aberration will counter, upon implantation in the eye, a positive spherical aberration of the cornea. Consequently, a residual spherical aberration of a human eye incorporating such a lens, as a combined optical system of the lens and cornea, can reach a desired value. As noted above, the spherical aberration of the human cornea can range from about 0.194 to 0.284 microns. That is, it can show a variation in a range of 0.09 microns. To avoid overcorrection, in many embodiments, the negative spherical aberration of the lens (which can range from about −0.202 microns to about −0.190 microns) can correct the low end of the range of corneal spherical aberration. As a result, in many embodiments, the residual spherical aberration of the eye, upon implantation of the IOL, can be larger than zero and less than about +0.14 microns (e.g., in a range from about +0.006 to about +0.09 microns). As discussed below, optical performance evaluations have shown that even with a residual spherical aberration of +0.14 microns, the aspheric IOL still outperforms a respective spherical lens. Such residual spherical aberration can be measured, e.g., in a model eye incorporating the lens and having an aspherical cornea model with a selected asphericity (e.g., one equal to an average corneal asphericity across a population). Alternatively, the residual spherical aberration can be measured in a natural eye in which the lens is implanted.

In some embodiments, the aspherical profile of the posterior surface can be defined in accordance with the following relation:

$$z = \frac{cr^2}{1+[1-(1+k)c^2r^2]^{\frac{1}{2}}} + a_1 r^2 + a_2 r^4 + a_3 r^6 \qquad \text{Eq. (1)}$$

wherein, z denotes a sag of the surface at a radial distance r from an optical axis of the lens, c denotes curvature of the surface at its apex (at the intersection of the optical axis with the surface); c=1/r where r denotes the radius of the surface at its apex, k denotes a conic constant, $a_1$ denotes a second order aspheric coefficient, $a_2$ denotes a fourth order aspheric coefficient, and $a_3$ denotes a sixth order aspheric coefficient.

In some embodiments, the optic can provide an optical power in a range of about 6 D to about 30 D, and an aspheric surface of the lens can be characterized by the above relation with c ranging from about 0.0152 mm$^{-1}$ to about 0.0659 mm$^{-1}$, k ranging from about −1162 to about −19, $a_1$ ranging from about −0.00032 mm$^{-1}$ to about −0.00020 mm$^{-1}$, $a_2$ ranging from about −0.0000003 (minus 3×10$^{-7}$) mm$^{-3}$ to about −0.000053 (minus 5.3×10$^{-5}$) mm$^{-3}$, and $a_3$ ranging from about 0.0000082 (8.2×10$^{-6}$) mm$^5$ to about 0.000153 (1.53×10$^{-4}$) mm$^{-5}$.

In other embodiments, the optic can provide an optical power in a range of about 16 D to about 25 D, and an aspheric surface of the lens can be characterized by the above relation with c ranging from about 0.0369 (1/27.1) mm$^{-1}$ to about 0.0541 (1/18.5) mm$^{-1}$, k ranging from about −73 to about −27, $a_1$ ranging from about −0.000209 mm$^{-1}$ to about −0.000264 mm$^1$, $a_2$ ranging from about −0.0000297 mm$^{-3}$ to about −0.0000131 mm$^{-3}$, and $a_3$ ranging from about 0.00000978 mm$^{-5}$ to about 0.00000846 mm$^{-5}$.

Although in this embodiment, the posterior surface of the optic includes an aspherical profile, in other embodiments, the anterior surface can be aspherical. Alternatively, a certain degree of asphericity can be imparted to both surfaces so as to achieve a desired negative spherical aberration suitable for countering a positive corneal spherical aberration.

In many embodiments, the anterior and posterior optical surfaces (and more particularly, their curvatures) are selected so as to impart a desired shape factor to the lens. As known in the art, the shape factor of a lens can be defined by the following relation:

$$\text{Shaper Factor } (X) = \frac{r_1 + r_2}{r_1 - r_2} \qquad \text{Eq. (2)}$$

wherein $r_1$ denotes a radius of one surface and $r_2$ that of the other (for an aspherical surface, the radius can be measured at its apex). Alternatively, for an aspherical surface, an average curvature (reciprocal of average radius) can be defined by the following relation:

$$C_{eff} = C_{base} + 2a_1 \qquad \text{Eq. (3)}$$

wherein, $C_{eff}$ denotes an effective curvature of the aspherical surface, $C_{base}$ denotes the curvature of the surface at its apex, and $a_1$ denotes the 2$^{nd}$ order even aspherical coefficient as defined above in Eq. (1).

The average curvature can be utilized, e.g., in calculation of the shape factor and the location of the lens's principal plane.

In many embodiments, the shape factor of the lens is selected to be in a range of about −0.016 to about 0.071, though other shape factors can also be employed.

Figure 2:
FIG. 2 is another side view of the lens of FIG. 1 illustrating a principal plane of the lens that is offset from a desired lens plane (HP)

With reference to FIG. 2, in some embodiments, the lens 10 includes a principal plane 22 that is offset relative to a desired lens plane such as the plane defined by the junctions of the two haptics and the optic (plane HP) by a selected distance, e.g., in a range of about −0.019 to about +0.018. In many embodiments, the location of the lens's principal plane relative to the haptics plane can be calculated in the following manner. The haptics plane located at the central-line of the lens edge will have a distance (HL) from the posterior surface apex specified by the following relation:

$$HL = Sag_2 + ET/2 \qquad \text{Eq. (4)}$$

wherein $Sag_2$ denotes the sag height of the posterior surface at the lens edge, and ET represents the IOL edge thickness. From the posterior surface apex, the relative location of the second principal plane can be obtained by the following relation:

$$PP_2 = \frac{-n_1 dF_1}{n_2 F_L} \qquad \text{Eq. (5)}$$

wherein $n_1$ and $n_2$ are, respectively, the refractive indices of a medium surrounding the lens and the material forming the lens, $F_1$ and $F_L$ are, respectively, the powers of the first surface (anterior surface) and the whole lens, and d is the IOL's central thickness. The location of the second principal point relative to the haptics plane (the anchor plane of the IOL) can therefore be obtained by the following relation:

$$\Delta PP_2 = HL + PP_2 = Sag_2 + \frac{ET}{2} - \frac{n_1 dF_1}{n_2 F_L} \quad \text{Eq. (6)}$$

wherein $\Delta PP_2$ denotes a offset change of the principal plane, and the other parameters are defined above.

By way of illustration, Table 1 below lists exemplary parameters (such as the radii of curvature of anterior and posterior surfaces, the asphericity coefficients of the posterior surface, as well as the center thickness of the lens) of a plurality of exemplary designs in accordance with some embodiments of the invention:

TABLE 1

| IOL Labeled power (Diopters) | spherical ant. radius $r_{1(mm)}$ | aspherical post apex $r_2$(mm) | center thickness $t_c$(mm) | edge thickness t (mm) | conic k | Even Asphericity Coefficients | | |
|---|---|---|---|---|---|---|---|---|
| | | | | | | 2$^{nd}$ order $a_1$ | 4$^{th}$ order $a_2$ | 6$^{th}$ order $a_3$ |
| 16.00 | 27.375 | −27.100 | 0.512 | 0.21 | −73.3310 | −2.0925E−04 | −2.9663E−05 | 9.7771E−06 |
| 16.50 | 25.754 | −27.100 | 0.522 | 0.21 | −73.3310 | −2.0952E−04 | −2.9663E−05 | 9.7771E−06 |
| 17.00 | 24.313 | −27.100 | 0.533 | 0.21 | −73.3310 | −2.0952E−04 | −2.9663E−05 | 9.7771E−06 |
| 17.50 | 23.025 | −27.100 | 0.543 | 0.21 | −73.3310 | −2.0952E−04 | −2.9663E−05 | 9.7771E−06 |
| 18.00 | 24.207 | −24.200 | 0.552 | 0.21 | −53.9988 | −2.1941E−04 | −2.5269E−05 | 9.3176E−06 |
| 18.50 | 22.929 | −24.200 | 0.563 | 0.21 | −53.9988 | −2.1941E−04 | −2.5269E−05 | 9.3176E−06 |
| 19.00 | 21.780 | −24.200 | 0.573 | 0.21 | −53.9988 | −2.1941E−04 | −2.5269E−05 | 9.3176E−06 |
| 19.50 | 20.739 | −24.200 | 0.584 | 0.21 | −53.9988 | −2.1941E−04 | −2.5269E−05 | 9.3176E−06 |
| 20.00 | 21.557 | −22.000 | 0.593 | 0.21 | −42.1929 | −2.3318E−04 | −2.1144E−05 | 8.9923E−06 |
| 20.50 | 20.537 | −22.000 | 0.603 | 0.21 | −42.1929 | −2.3318E−04 | −2.1144E−05 | 8.9923E−06 |
| 21.00 | 19.609 | −22.000 | 0.614 | 0.21 | −42.1929 | −2.3318E−04 | −2.1144E−05 | 8.9923E−06 |
| 21.50 | 18.761 | −22.000 | 0.624 | 0.21 | −42.1929 | −2.3318E−04 | −2.1144E−05 | 8.9923E−06 |
| 22.00 | 19.583 | −20.000 | 0.633 | 0.21 | −33.2270 | −2.4979E−04 | −1.6772E−05 | 8.6957E−06 |
| 22.50 | 18.737 | −20.000 | 0.644 | 0.21 | −33.2270 | −2.4979E−04 | −1.6772E−05 | 8.6957E−06 |
| 23.00 | 17.961 | −20.000 | 0.654 | 0.21 | −33.2270 | −2.4979E−04 | −1.6772E−05 | 8.6957E−06 |
| 23.50 | 17.246 | −20.000 | 0.665 | 0.21 | −33.2270 | −2.4979E−04 | −1.6772E−05 | 8.6957E−06 |
| 24.00 | 17.781 | −18.500 | 0.673 | 0.21 | −27.4571 | −2.6429E−04 | −1.3133E−05 | 8.4634E−06 |
| 24.50 | 17.080 | −18.500 | 0.684 | 0.21 | −27.4571 | −2.6429E−04 | −1.3133E−05 | 8.4634E−06 |
| 25.00 | 16.482 | −18.500 | 0.695 | 0.21 | −27.4571 | −2.6429E−04 | −1.3133E−05 | 8.4634E−06 |
| 25.50 | 16.831 | −18.500 | 0.705 | 0.21 | −27.4571 | −2.6429E−04 | −1.3133E−05 | 8.4634E−06 |

Figure 3:
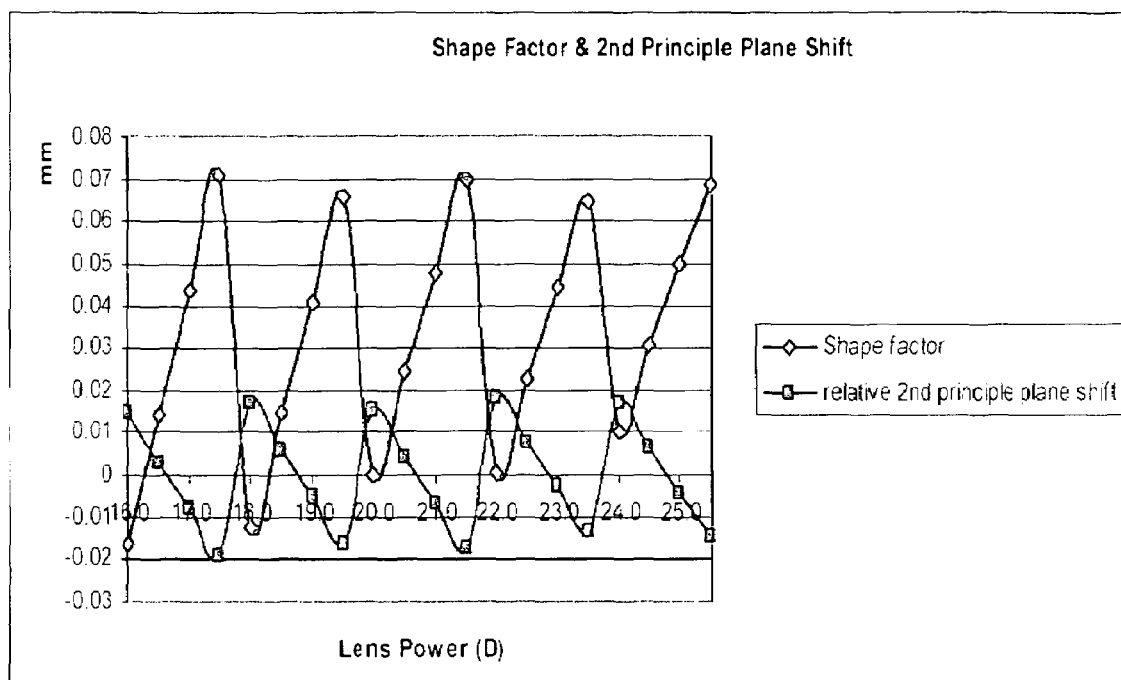
FIG. 3 depicts graphs illustrating variations of shape factor and principal plane shift of a plurality of exemplary theoretically designed lenses as a function of lens power over a power range of about 16 D to about 25 D.

By way of further example, FIG. 3 depicts variations of the shape factor and principal plane shift as a function of optical power of the lens in the embodiments of the lens 10 having the parameters listed in the above Table 1.

To show the efficacy of aspherical IOLs of the invention in providing enhanced optical performance, the image quality obtained by such an IOL was theoretically investigated by employing the Alcon-Navarro model eye—Navarro model eye was modified to have an aspheric cornea model—for corneas having a range of aberrations. The image quality was evaluated by calculating modulation transfer functions (MTFs) exhibited by the model eye at a wavelength of 550 nm for cornea models having average human spherical aberration as well as for cornea models in which the corneal spherical aberrations deviate by +/−1 standard deviation from the average aberration. In addition, the MTF exhibited by a similar lens that lacks asphericity was also calculated for comparison with that of the aspherical lens. As known to those having ordinary skill in the art, the MTF provides a quantitative measure of image contrast exhibited by an optical system, e.g., a system formed of an IOL and the cornea. More specifically, an MTF of an imaging optical system, such as a lens, can be defined as a ratio of a contrast associated with an image of an object formed by the optical system relative to a contrast associated with the object.

The corneal parameters utilized for the above MTF calculations are summarized in Table 2 below:

TABLE 2

| | Cornea −1 standard deviation away from mean | Mean Cornea | Cornea +1 standard deviation away from mean |
|---|---|---|---|
| Spherical Aberration | 0.155 microns | 0.241 microns | 0.327 microns |
| Conic Constant | −0.384 | −0.183 | −0.059 |

The optical power of both the aspherical and spherical lenses was selected to be 22 D in an aqueous surrounding medium having an index of refraction of 1.336. The anterior surfaces of both lenses exhibited the same radius of curvature. And the radii of curvature at the apex of the posterior surfaces were also identical. However, the posterior surface of the aspherical lens exhibited a degree of asphericity (characterized by a conic constant of about −33). The MTFs were calculated at the focal plane of the model eye for both a 3 mm and a 5 mm pupil.

Figure 4A:
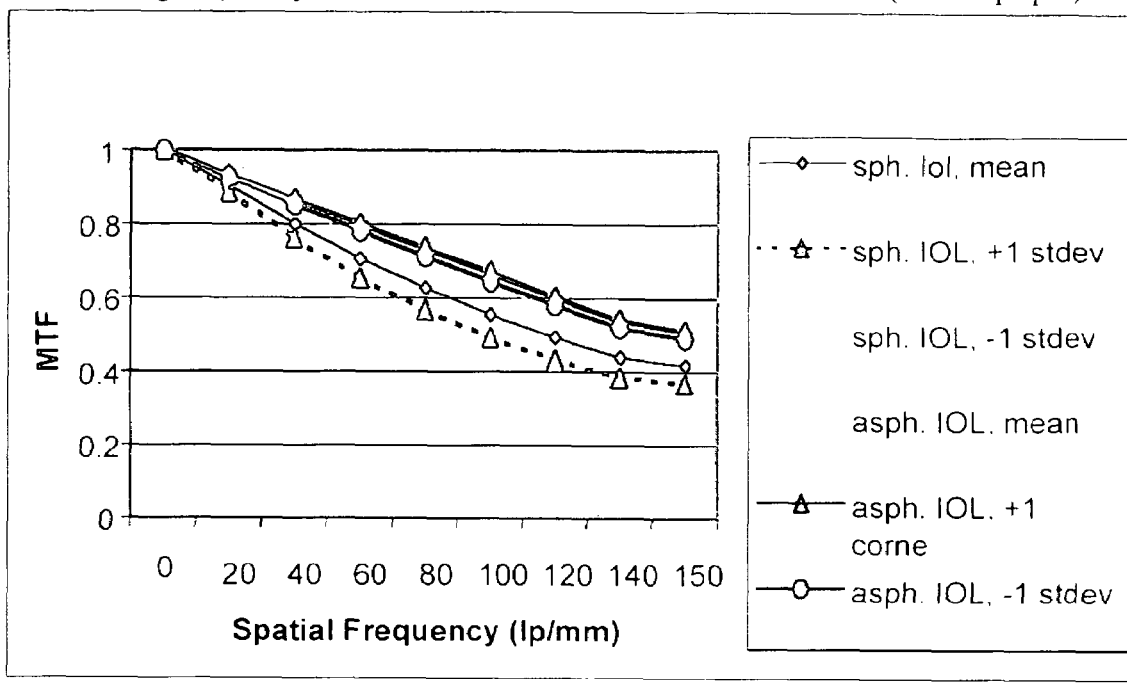
FIG. 4A shows a plurality of MTF curves calculated for model eyes having a spherical and an aspherical lens for a plurality of different corneal asymmetries at a pupil size of 3 mm.
Figure 4B:
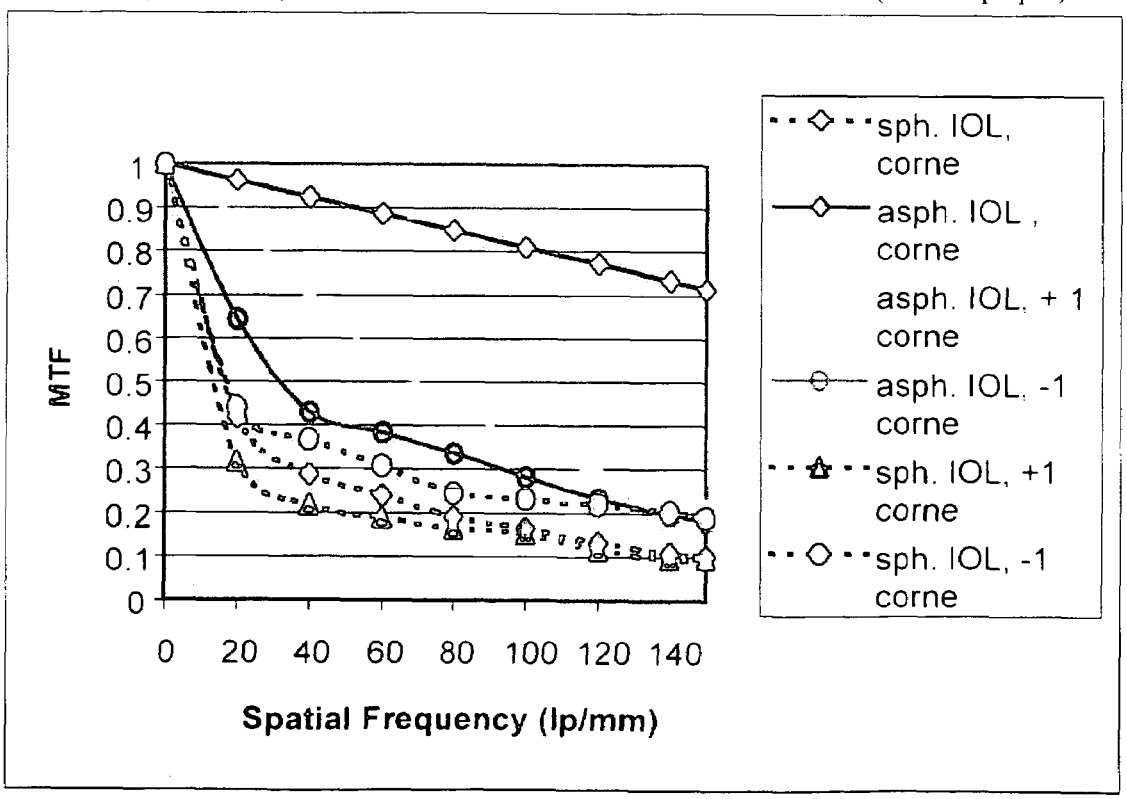
FIG. 4B shows a plurality of MTF curves calculated for model eyes having a spherical and an aspherical lens for a plurality of different corneal asymmetries at a pupil size of 5 mm.

FIG. 4A shows a plurality of MTF curves calculated for the spherical and the aspherical lenses for the aforementioned corneal models at a 3 mm pupil size while FIG. 4B depicts MTF curves calculated for those lenses and corneal models at a 5 mm pupil size. For both the 3 mm and 5 mm pupil sizes, the aspherical lens exhibits an enhanced performance relative to that of the spherical lens. It is worth noting that even with a model cornea that has a positive spherical aberration of 0.327 microns (Table 2), the aspheric lens shows MTF improvement over the spherical lens. In this case, the residual spherical aberration of the combined cornea and the lens model is about +0.14 microns (i.e., cornea's spherical aberration of 0.327 microns+lens's spherical aberration of −0.190 microns=0.137 (about 0.14) microns combined spherical aberration). Hence, the beneficial residual spherical aberration can be up to +0.14 microns in an eye implanted with an ophthalmic lens. It should be understood that the aforementioned MTF curves are provided only for illustrative purposes, and not to necessarily indicate optimal performance exhibited by lenses of the invention.

The range of negative spherical aberrations exhibited by the IOLs of the invention render their optical performance less susceptible to misalignments, such as tilt and/or decentration, relative to traditional aspheric lenses. In other words, the values of asphericity imparted to the IOLs of the invention allows them to provide a more robust performance relative to traditional aspheric lenses.

A variety of lens design tools and lens manufacturing techniques can be employed to design and manufacture aspherical lenses in accordance with the teachings of the invention. By way of example and only for illustration purposes, a procedure utilized to design a plurality of lenses with an optical power in a range of about 16 D to about 25 D is discussed in the following example. It should be understood that this design procedure is described to further illustrate different aspects of the invention, and is not intended to be limiting of the scope of the invention.

EXAMPLE

A plurality of aspherical lenses were theoretically designed within a power range of 16 D to 25 D by dividing the power range into five bands with power increments of 2 D. In these exemplary designs, the posterior surface of the lens was assumed to exhibit an aspherical profile. The following lens equation was employed to derive the radius of the spherical anterior surface and the apex radius of the aspherical posterior surface:

$$D = \frac{n_1 - n_{med}}{r_a} + \frac{n_1 - n_{med}}{r_p} - \frac{t_c}{n_1 * \left(\frac{n_1 - n_{med}}{r_a}\right) * \left(\frac{n_1 - n_{med}}{r_p}\right)}$$ Eq. (7)

wherein,
D denotes the optical power of the lens,
$n_1$ denotes the refractive index of the lens material,
$n_{med}$ denotes the refractive index of the medium surrounding the lens,
$r_a$ denotes the radius of the anterior surface,
$r_p$ denotes the radius of the posterior surface, and
$t_c$ denotes the center thickness of the lens.

The apex radius of the posterior surface was fixed within one band and the anterior radius was calculated using known (desired) lens power, edge thickness, refractive index of the material forming the lens as well as the posterior surface radius. To satisfy design requirements for shape factor and principal plane shift, the fixed posterior apex radius was initially estimated and then adjusted within each of the five bands. For the aspherical portion of the design, the posterior apex radius was fixed and then the peripheral radius was aspherized (e.g., the peripheral radius was gradually increased from the center to the edge) to meet an aberration compensation requirement that was selected for each band. Accordingly, the shape factor and the principal plane shift were recalculated by changing the apex radius to an "effective" radius, which incorporated the apex radius and the $2^{nd}$ order aspherical coefficient (see Eq. (3)). The above Equation (2) was employed for calculating the lens's shape factor and the following relation was utilized to the principal plane shift (PPS):

$$PPS = \frac{D*(n_1 - n_{med})}{r_a} * \frac{n_{med}}{n_1} * t$$ Eq. (8)

wherein,
D denotes the optical power of the lens,
$n_1$ denotes the refractive index of the lens material,
$n_{med}$ denotes the refractive index of the material surrounding the lens,
$r_a$ denotes the radius of the anterior surface, and
t denotes the center thickness of the lens.

As a fixed edge thickness constraint was applied in each lens design, the lens's center thickness had to be adjusted, subsequent to optimizing the aspherical profile, to maintain the edge thickness constraint. To this end, the IOL center thickness was calculated by employing a lens design ray tracing software marketed under the trade designation Zemax® (version Mar. 4, 2003, Zemax Development Corporation, San Diego, Calif.). Further, a modified "effective" posterior radius was used instead of the apex radius because the $2^{nd}$ order aspherical coefficient also made a contribution to the first order optical property and hence affected the calculation of the principal plane. The design shape factor ranged from about −0.016 to about +0.071, and the relative principal plane shift change ranged from about −0.019 mm to about +0.018 mm across the power range.

The Zemax® optical design program was used for the aspherical design of the posterior surface. The radii calculated by the aforementioned lens equation were the starting points. The system pupil stop was set as 5 mm at the anterior surface of the IOL, which is equivalent to about 6 mm at the corneal plane. The focal point of the system was constrained at the paraxial focus, while the aspherical parameters of the IOL posterior surface comprised the only variables that were adjusted. An error function for the optimization was constructed as the root-mean-square (RMS) wavefront error with the designated raytracing intersection pattern. In its optimization cycle, Zemax® design program systematically adjusted the aspherical coefficients until the error function reached a minimum. Since in each band only one universal posterior design was utilized, the optimization was performed only for the mid-power value in that band (e.g., for 17 D in the band extending from 16 D to 17.5 D, or for 19 D in a band extending from 18 D to 19.5 D). For each band, the optical performance was checked at the two ends of that band to ensure that the design criteria were met. The above Table I lists the parameters of a plurality of lenses designed in this manner.

Those having ordinary skill in the art will appreciate that various changes can be made to the above embodiments without departing from the scope of the invention.

What is claimed is:

1. An ophthalmic lens, comprising
   an optic having an anterior surface and a posterior surface, said optic providing an optical power in a range of about 16 D to about 25 D,
   wherein at least one of said surfaces is characterized by an aspherical base profile such that said optic exhibits a negative spherical aberration in a range of about −0.202 microns to about −0.190 microns across said power range.

2. The ophthalmic lens of claim 1, wherein said aspherical base profile is characterized by a conic constant in a range of about −73 to about −27.

3. The ophthalmic lens of claim 1, wherein said aspherical base profile is defined by the following relation:

$$z = \frac{cr^2}{1 + [1 - (1+k)c^2r^2]^{\frac{1}{2}}} + a_1r^2 + a_2r^4 + a_3r^6$$

wherein,
z denotes a sag of the surface at a radial distance r from an optical axis of the lens,
c denotes curvature of the surface at its apex (at the intersection of the optical axis with the surface)
k denotes a conic constant,
$a_1$ denotes a second order aspheric coefficient,
$a_2$ denotes a fourth order aspheric coefficient, and
$a_3$ denotes a sixth order aspheric coefficient,
wherein c ranges from about 0.0369 (1/27.1) mm$^{-1}$ to about 0.0541 (1/18.5) mm$^{-1}$, k ranging from about −73 to about −27, $a_1$ ranging from about −0.000209 mm$^{-1}$ to about −0.000264 mm$^{-1}$, $a_2$ ranging from about −0.0000297 mm$^{-3}$ to about −0.0000131 mm$^{-3}$, and $a_3$ ranging from about 0.00000978 mm$^{-5}$ to about 0.00000846 mm$^{-5}$.

4. The ophthalmic lens of claim 1, wherein said optic exhibits a shape factor in a range of about −0.016 to about 0.071.

5. The ophthalmic lens of claim 1, wherein said optic comprises a biocompatible polymeric material.

6. The ophthalmic lens of claim 5, wherein the polymeric material is selected from the group consisting of acrylic, silicone and hydrogel materials.

7. The ophthalmic lens of claim 1, wherein said ophthalmic lens comprises an IOL.

8. An ophthalmic lens, comprising
an optic having an anterior surface and a posterior surface, said optic providing an optical power in a range of about 16 D to about 25 D, said optic having a principal plane exhibiting an offset change in a range of about −0.019 mm to about +0.018 mm from a selected plane of said optic,
wherein at least one of said surfaces is characterized by an aspherical base profile such that the optic exhibits a negative spherical aberration in a range of about −0.202 microns to about −0.190 microns across said power range.

9. The ophthalmic lens of claim 8, wherein said optic comprises a plurality of haptics coupled thereto, and said selected plane comprises a plane defined by junctions of said haptics and said optic.

10. The ophthalmic lens of claim 8, wherein said ophthalmic lens comprises an IOL.

11. An ophthalmic lens, comprising
an optic having an anterior surface and a posterior surface, said optic providing a nominal optical power in a range of about 16 D to about 25 D,
wherein at least one of said surfaces exhibits an aspheric base profile to provide a negative spherical aberration for countering, upon implantation in the eye, a positive spherical aberration of the cornea such that an optical system comprising the lens and cornea exhibits a residual positive spherical aberration less than about +0.14 microns.

12. The ophthalmic lens of claim 11, wherein said residual spherical aberration lies in a range of about +0.006 to about +0.09 microns.

13. The ophthalmic lens of claim 11, wherein said aspheric base profile is characterized by a conic constant in a range of about −73 to about −27.

14. The ophthalmic lens of claim 11, wherein said optic exhibits a shape factor in a range of about −0.016 to about 0.071.

15. The ophthalmic lens of claim 14, wherein said lens comprises an IOL.

16. The ophthalmic lens of claim 11, wherein said optic comprises a soft acrylic polymeric material.

17. The ophthalmic lens of claim 11, wherein said lens comprises an IOL.

18. An ophthalmic lens, comprising
an optic having a refractive anterior surface and a refractive posterior surface,
said surfaces cooperatively providing an optical power in a range of about 16 D to about 25 D,
wherein a profile of at least one of said surfaces is characterized in accordance with the following relation:

$$z = \frac{cr^2}{1 + [1 - (1+k)c^2r^2]^{\frac{1}{2}}} + a_1r^2 + a_2r^4 + a_3r^6$$

wherein,
z denotes a sag of the surface at a radial distance r from an optical axis of the lens,
c denotes curvature of the surface at its apex (at the intersection of the optical axis with the surface)
k denotes a conic constant,
$a_1$ denotes a second order aspheric coefficient,
$a_2$ denotes a fourth order aspheric coefficient, and
$a_3$ denotes a sixth order aspheric coefficient,
wherein c ranges from about 0.0369 (1/27.1) mm$^{-1}$ to about 0.0541 (1/18.5) mm$^{-1}$, k ranges from about −73 to about −27, $a_1$ ranges from about −0.000209 mm$^{-1}$ to about −0.000264 mm$^{-1}$, $a_2$ ranges from about −0.0000297 mm$^{-3}$ to about −0.0000131 mm$^{-3}$, and $a_3$ ranges from about 0.00000978 mm$^{-5}$ to about 0.00000846 mm$^{-5}$.

* * * * *